United States Patent [19]

Caggiani et al.

[11] Patent Number: 4,842,592
[45] Date of Patent: Jun. 27, 1989

[54] CONNECTOR ASSEMBLY

[75] Inventors: Carlos A. Caggiani; Thomas A. Coneys, both of Peterborough; Kenneth W. Larson, Keene, all of N.H.

[73] Assignee: Teleflex Incorporated, Limerick, Pa.

[21] Appl. No.: 163,170

[22] Filed: Feb. 26, 1988

Related U.S. Application Data

[63] Continuation of Ser. No. 47,842, May 6, 1987, abandoned, which is a continuation of Ser. No. 607,295, May 4, 1984, abandoned.

[51] Int. Cl.[4] .............................................. A61M 5/00
[52] U.S. Cl. ................................... 604/283; 285/334.2
[58] Field of Search .............. 604/245, 243, 280, 283, 604/905, 165; 285/334.2, 334.3, 397

[56] References Cited

U.S. PATENT DOCUMENTS

| | | | |
|---|---|---|---|
| 3,766,916 | 10/1973 | Moorehead et al. | 604/165 |
| 3,917,403 | 8/1976 | Patel | 604/280 |
| 4,187,846 | 2/1980 | Lolachi et al. | 604/905 |
| 4,187,848 | 2/1980 | Taylor | 604/243 |
| 4,252,122 | 2/1981 | Halvorsen | 604/905 |
| 4,256,106 | 3/1981 | Shoor | 604/905 |
| 4,326,519 | 4/1982 | D'Alo et al. | 604/165 |
| 4,418,945 | 12/1983 | Kellogg | 604/905 |
| 4,613,329 | 9/1986 | Bodicky | 604/158 |

*Primary Examiner*—Stephen C. Pellegrino
*Attorney, Agent, or Firm*—Weiser & Stapler

[57] ABSTRACT

An adaptive connector assembly for engaging a catheter or the like comprises a pair of segments adapted for telescoping engagement with one another so as to develop a centrally disposed cavity for receiving a plug formed of a compressible material. An end of one of the segments has an opening which communicates with the cavity and which is adapted to receive the catheter therein. The plug also has a centrally disposed channel for receiving the catheter from the opening. A snap-fit engagement is developed between the telescoping segments so that when the telescoping segments are engaged, the plug is placed in compression, constricting the channel about the catheter and thereby engaging the catheter within the adaptive connector assembly.

44 Claims, 2 Drawing Sheets

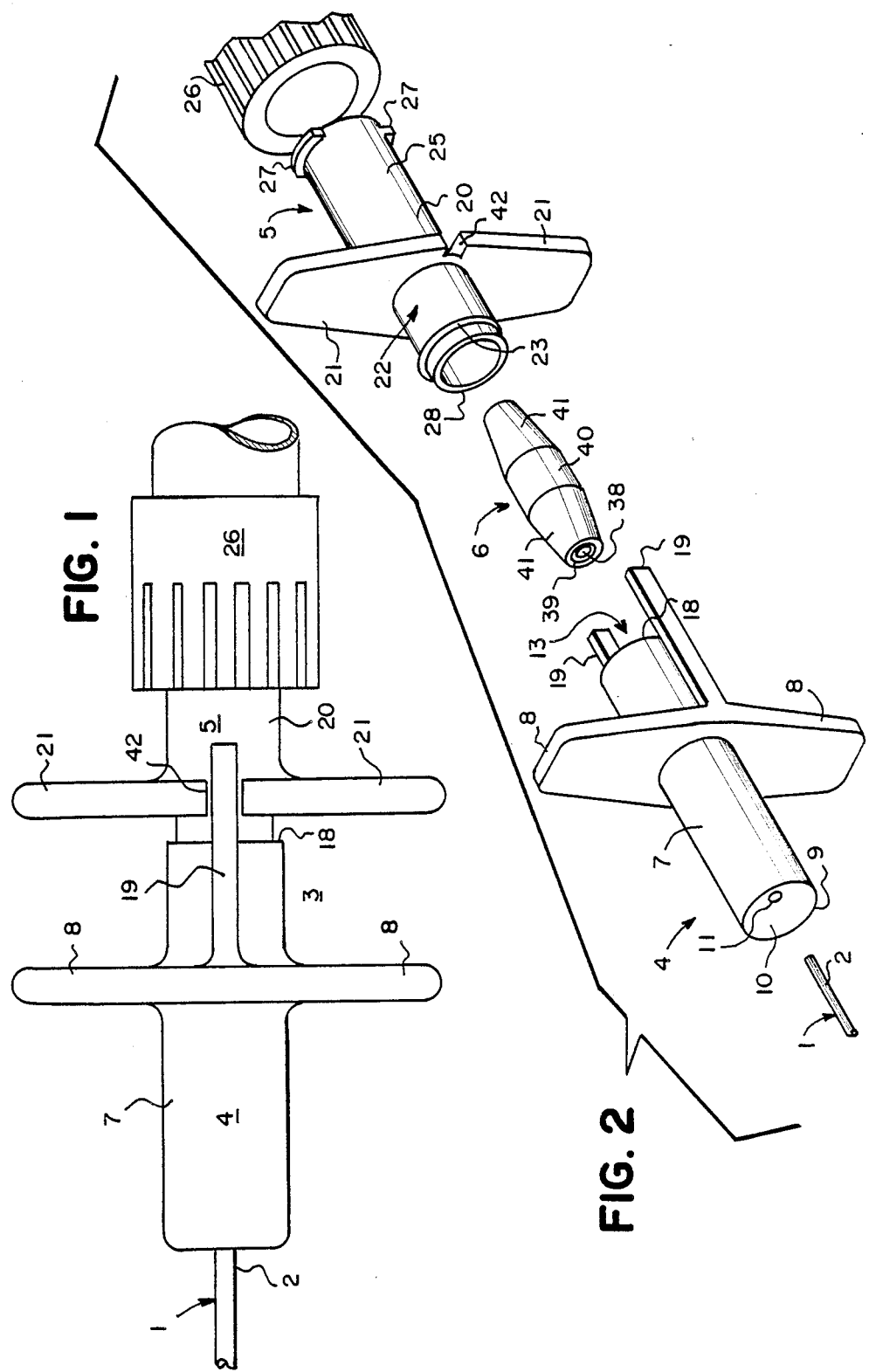

CONNECTOR ASSEMBLY

This application is a continuation of application Ser. No. 047,842, filed May 6, 1987 now abandoned, which is a continuation of application Ser. No. 607,295, filed May 4, 1984, now abandoned.

BACKGROUND OF THE INVENTION

The present invention relates generally to adaptive connector assemblies, and in particular, to adaptive connector assemblies which are particularly well-suited to medical applications.

A number of medical procedures involve the catheterization of patients for various reasons. One such application is the administration of anesthesia either in advance of, or during a particular medical procedure. Often, anesthesia must be administered continuously, or at regular intervals, to maintain the effects of the anesthesia during an extended medical procedure. Other such applications include various vascular procedures, various intra-uterine procedures, transfusions, etc. The present application is generally directed to a connector assembly for use in connection with such procedures, particularly those requiring catheterization by means of the so-called "through the needle" introduction technique.

This technique generally involves the use of a needle which is capable of being suitably positioned in a patient's body so as to enable an appropriate, generally flexible catheter to be threaded through the needle so that a distal end of the catheter is appropriately lodged in position within the patient's body, and so that a proximal end of the catheter is capable of extending from the patient's body. After appropriate positioning of the catheter, the needle is removed from the patient's body in a manner which allows the distal portions of the catheter to remain in position as required, and which permits the proximal portions of the catheter to freely extend from the patient's body so that subsequent movement of the patient will not cause the distal portions of the catheter to become dislodged from the patient. Anesthetic or other desired medicaments are then capable of being appropriately introduced to the patient by means of the catheter in conventional fashion.

Of course, in order to enable convenient use of the catheter, it is important that the proximal end of the catheter be provided with an appropriate connector assembly which securely engages the proximal end of the catheter, and enables appropriate medical equipment (syringes, infusion devices, etc.) to be selectively connected to the catheter during the medical procedure in progress. Since such connector assemblies would be disruptive of the catheterization procedure in view of their size and shape, it is therefore necessary that such connector assemblies be attachable to the catheter after positioning in the patient's body.

A variety of connector assemblies have been developed to provide this function. Generally, such connectors make use of a hollow cylindrical body having an aperture at one end for receiving the catheter, and a cap at the other end which threadingly engages the cylinder and which also includes a connector for attachment to appropriate medical equipment, as desired. Positioned within the cylinder is a compressible pellet or plug having a centrally disposed aperture which is capable of passing the catheter through the resulting assembly. Upon placement of the catheter within the cylinder and through the plug which it contains, tightening of the cap with respect to the cylinder causes a compression of the plug which is capable of retaining the catheter within the connector assembly so that the open end of the catheter is exposed to the connector, enabling its connection to medical equipment, as appropriate. Examples of such devices may be had with reference to U.S. Pat. Nos. 4,419,094 and 4,187,848, among others.

Although effective in operation, certain difficulties have been encountered in using such connector assemblies. For example, it will be noted that engagement of the catheter by the compressible plug is primarily dependent upon a threaded fitting. This leads to two complications in operation.

First, a threaded fitting is continuously adjustable. This often leads to undertightening or overtightening of the cap with respect to the cylinder. Undertightening can cause the connector assembly to become dislodged from the catheter, necessitating reattachment of the connector assembly to the catheter, often at times during the medical procedure which are at least inconvenient, and quite possibly inappropriate. Overtightening can cause undue compression of the plug, leading to a partial or total occlusion of the catheter, a condition which is clearly unacceptable and which is often not easily detected until the catheter is ultimately called into use.

Second, in tightening the cap with respect to the cylinder, particularly in connection with an overtightening, it is possible for the torsion which develops between the cap and the plug to twist the plug within the cylinder. At times, this can cause twisting of the catheter within the connector assembly. Again, this can lead to an unacceptable partial occlusion. In extreme cases, this can lead to a complete occlusion, or even damage to the catheter. The latter result can necessitate replacement of the catheter, a condition which is clearly undesirable. Although washers have been positioned between the cap and plug to serve as compression bushings in an effort to eleviate such problems, the results achieved have not proved to be entirely satisfactory.

Also to be considered are certain difficulties in attaching such conventional connector assemblies to the catheter. For example, it is often difficult to properly thread the catheter through the various elements which comprise the connector assembly, particularly when offset apertures are provided to achieve secure catheter retention. This problem is amplified as the number of internal components are increase, such as when compression washers are used to ameliorate the problems of torsioning as previously described. It is therefore not uncommon for improperly aligned components of the connector assembly to impede threading of the catheter through the connector assembly, at times leading to damage of the proximal end of the catheter upon attempting its attachment to the connector assembly (kinking, bending, crimping, twisting, etc.).

Another difficulty arises from the need to appropriately locate the proximal end of the catheter within the connector assembly so that sufficient portions of the catheter are available for secure engagement, but so that the open end of the catheter is correctly positioned within the connector assembly in a manner which correctly exposes the opening to the medical equipment which is to be attached to the connector assembly. Thus, proper placement of a catheter within the connector assembly will require sufficient penetration of the catheter into the connector assembly, to assure satisfactory engagement, while avoiding overextension of the open end of the catheter into the connector assembly, which could interfere with the attachment of medical equipment to the connector. Moreover, such positioning must be developed as the cap is rotated with respect to the cylinder for tightening. This requires three discrete operations (catheter placement, cylinder retention, cap rotation) which are often not easily accomplished by hand, the conventional manner of assembling such components.

It has therefore remained to develop a connector assembly which is simple and reliable in use, and which does not exhibit the foregoing disadvantages.

SUMMARY OF THE INVENTION

It is therefore a primary object of the present invention to provide an improved connector assembly which is primarily intended for use in conjunction with catheterization procedures.

It is also an object of the present invention to provide a connector assembly which is simple in construction and easy in use.

It is also an object of the present invention to provide a connector assembly which does not rely upon threaded members for catheter engagement.

It is also an object of the present invention to provide a connector assembly which is not subject to overtightening and undertightening of the catheter within the connector assembly.

It is also an object of the present invention to provide a connector assembly which avoids the difficulties of overtightening and undertightening by providing a precise means for automatically regulating tightening of the connector assembly against the catheter.

It is also an object of the present invention to provide a connector assembly which incorporates internal components which are not subject to torsioning.

It is also an object of the present invention to provide a connector assembly which promotes threading of the catheter within the connector assembly.

It is also an object of the present invention to provide a connector assembly which facilitates proper positioning of the catheter within the connector assembly, including correct penetration.

It is also an object of the present invention to provide a connector assembly which is capable of single-handed operation, enabling attachment of a connector assembly and a catheter to be readily accomplished using two hands.

These and other objects are achieved in accordance with the present invention by providing a connector assembly which generally incorporates two cooperating segments which are telescopically positioned within one another so as to develop a cavity which is capable of receiving a compressible plug therein. The plug, and the cavity which engages it, are correspondingly configured in a manner which develops uniform compression of the plug against the catheter along the centrally disposed aperture which engages the catheter. The telescoping segments are provided with means for developing a snap-fit interengagement between the segments which automatically assures appropriate compression of the plug within the cavity without the use of threaded components. The segments of the connector assembly, and the plug which they contain, are further configured so that insertion of a catheter into the connector assembly, and compression of the connector assembly so that the telescoping segments engage one another by means of the snap-fit arrangement provided, automatically assures correct placement of the catheter within the connector assembly, and correct tightening of the connector assembly against the catheter.

For further detail regarding a preferred embodiment connector assembly in accordance with the present invention, reference is made to the following detailed description taken in conjunction with the following illustrations.

BRIEF DESCRIPTION OF THE DRAWINGS

FIG. 1 is an elevational view of the proximal end of a completed catheterization, showing the connector assembly interconnecting a catheter with medical equipment for introducing medicaments to a patient.

FIG. 2 is an exploded view, in perspective, of the connector assembly illustrated in FIG. 1.

In the several view provided, like reference numerals denote similar structure.

DETAILED DESCRIPTION OF THE PREFERRED EMBODIMENT

Figure 3:
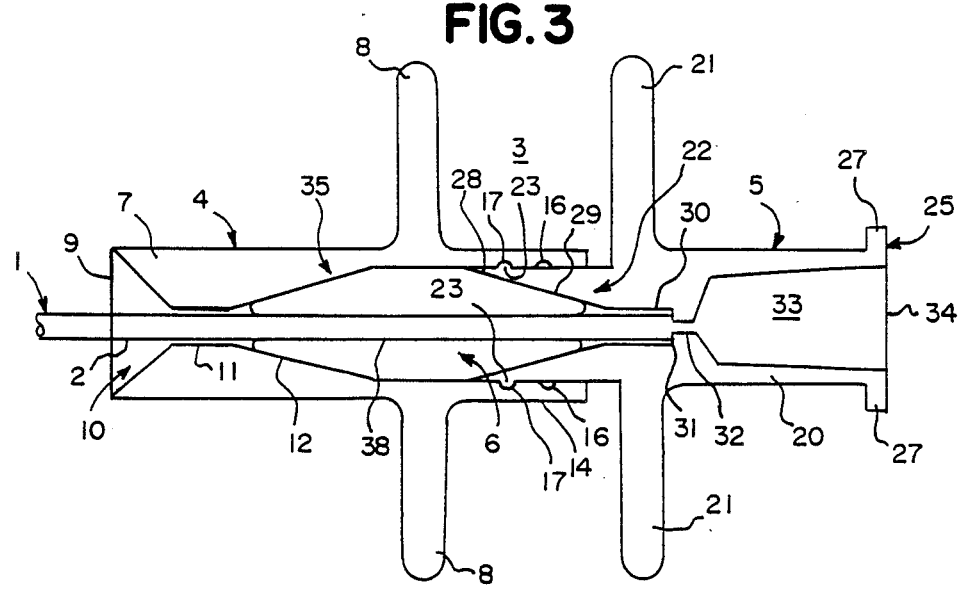
FIG. 3 is a cross-sectional view of the connector assembly illustrated in FIG. 1, omitting the medical equipment.

Although specific forms of the invention have been selected for illustration in the drawings, and the following description is drawn in specific terms for the purpose of describing these forms of the invention, this description is not intended to limit the scope of the invention which is defined in the appended claims.

FIG. 1 exemplifies portions of a catheterization procedure wherein distal portions (not shown) of a catheter 1 have been suitably positioned within a patient so that the catheter extends from the patient in desired fashion, exposing the proximal end 2 of the catheter 1 for appropriate engagement to a connector assembly 3 in accordance with the present invention. It will be understood that the catheter 1 shown in the drawings has only been provided for illustrative purposes, and that any of a number of available catheters may be used in conjunction with the connector assembly 3 of the present invention to accomplish any of a number of medical procedures, as desired.

With reference to FIGS. 2 and 3, the connector assembly 3 generally comprises a pair of interengaged segments 4, 5 which cooperate with a centrally contained plug 6 to engage the proximal end 2 of the catheter 1 to the connector assembly 3 as will be more fully described below.

A first segment 4 of the connector assembly 3 generally comprises a cylindrical body 7 having a pair of finger grips 8 extending transversely outwardly from its surface at opposing edges. Central portions of the body 7 are reliefed in specified fashion, as follows. Progressing from left to right in FIG. 3, the end 9 of the body 7 incorporates a shaped, generally conical, recess 10 which terminates at a narrowed opening 11 having a diameter which is appropriate for slidingly receiving the catheter 1 as will be more fully described below. The catheter receiving opening 11 then expands progressively outwardly at 12, developing a generally conical taper which opens into a generally cylindrical cavity 13 defined by the outer wall 14 of the body 7. The wall 14 is provided with two circumferentially disposed detents 16, 17 located at spaced intervals along the wall 14 as will be described more fully below. The cavity 13 is open ended at the edge 18 of the body 7. A pair of guides 19 extend longitudinally from opposing sides of the edge 18 of the body 7, being offset in relation to the center axis of the body 7.

A second segment 5 of the connector assembly 3 also generally comprises a cylindrical body 20 having a pair of finger grips 21 extending transversely outwardly from its surface at opposing edges. The end 22 of the body 20 which is to cooperate with the segment 4 is provided with an outer diameter which substantially equals the diameter of the cavity 13 of the segment 4 so as to enable sliding, telescoping engagement between the end 22 of the segment 5 and the cavity 13 of the segment 4. The outer surface of the end 22 of the body 20 further incorporates a ring 23 which extends circumferentially about the body 20, and which is correspondingly sized to be received within the detents 16, 17 of the cavity 13 as will be described more fully below. The outer surface of the end 25 of the body 20 which is opposite to the end 22 is suitably configured to receive a connector 26 of any of a variety of conventionally available medical devices, including those which make use of Luer-type connectors, and others. To this end, the end 25 of the body 20 is provided with an outer diameter which will suitably receive the connector 26 used, and incorporates a pair of outwardly extending lugs 27 for engaging the connector 26 in suitable fashion.

Central portions of the body 20 are again reliefed in specified fashion, as shown. To this end, progressing from left to right, the end 28 of the body 20 converges progressively inwardly at 29, to develop a generally conical taper which terminates at a narrowed opening 30 having a diameter which is appropriately sized to slidingly receive the catheter 1 as will be more fully described below. The narrowed opening 30 terminates at a stop 31 which defines the opening of a channel 32 having a diameter which is less than the diameter of the narrowed opening 30, and the outer diameter of the catheter 1, for purposes which will be described more fully below. Thereafter, the channel 32 expands outwardly into a cavity 33 which communicates with the open outer end 34 of the body 20.

Upon assembly, the body 20 of the segment 5 is inserted into the cavity 13 of the segment 4, cooperating with the body 7 of the segment 4 to develop a shaped cavity 35 for receiving the plug 6, which is formed of an elastomeric material such as a natural rubber, a thermoplastic rubber, a silicone rubber, or another appropriate polymer. The plug 6 is symmetrically shaped and includes a generally cylindrical center 36 separating a pair of tapered ends 37. Axially disposed within the plug 6 is a channel 38 having a diameter sized to receive the catheter 1 as will be described more fully below. The ends of the channel 38 are provided with chamfers 39 to assist in insertion of the catheter 1. It will be noted that the cavity 35 developed upon interconnecting the segments 4, 5 incorporates a cylindrical portion 40 which is configured to substantially correspond to the cylindrical center 36 of the plug 6, and tapered portions 12, 29 which are each configured to substantially correspond with the tapered ends 37 of the plug 6. Accordingly, upon assembly of the segments 4, 5 (preferably formed of a suitable rigid polymeric material) in combination with a plug 6, the plug 6 will be securely retained within the cavity 35 so that the channel 38 is in substantial axial alignment with the opening 11 of the segment 4 and the opening 30 of the segment 5.

Figure 4:
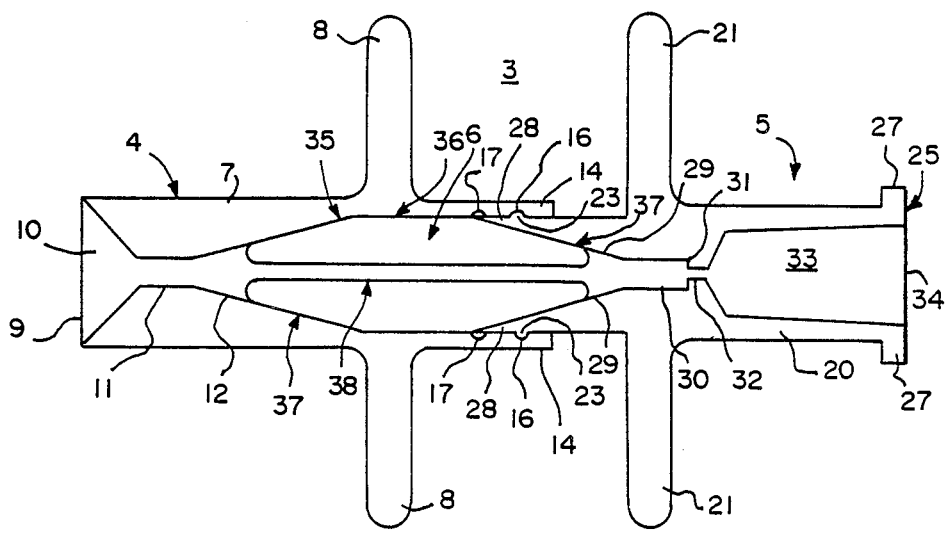
FIG. 4 is a cross-sectional view of the connector assembly in a stand-by position assumed in developing the catheterization illustrated in FIG. 1.

With reference to FIG. 4, it will be noted that upon assembly of the foregoing components, the body 20 of the segment 5 will be telescopically retained within the body 7 of the segment 4 so that the rib 23 of the body 20 engages the detent 16 of the body 7, and so that the guides 19 extend through a pair of slots 42 provided in the finger grips 21 of the segment 5. In this position, which constitute a stand-by position of operation, the plug 6 will be retained within the cavity 35 so that the cylindrical center 36 of the plug 6 is in substantial contact with the cylindrical portion 40 of the cavity 35, and so that the tapered ends 37 of the plug 6 are in substantial contact with the tapered portions 12, 29 of the cavity 35. Preferably, this interengagement is such that the plug 6 substantially completely fills the cavity 35, but is not placed in compression. Maintenance of this stand-by positioning is established by the interaction which is developed between the rib 23 of the detent 16. Respective rotation between the segments 4, 5 is prevented by means of the interaction which is developed between the guides 19 of the segment 4 and the slots 42 of the segment 5.

In use, the proximal end 2 of the catheter 1 is inserted into the opening 11 of the segment 4, tapering of the recess 10 assisting in such placement. The proximal end 2 is further slidingly advanced through the opening 11 and to the channel 38 of the plug 6, the length of the channel 11 assisting in assured engagement of the channel 38. In the stand-by position, the channel 38 of the plug 6 is relaxed so as to enable passage of the proximal end 2 of the catheter 1 through the plug 6, the chamfers 39 assisting in such placement. After leaving the channel 38, the proximal end 2 of the catheter 1 enters the opening 30 of the segment 5. Upon encountering the stop 31, further movement of the proximal end 2 of the catheter 1 into the connector assembly 3 is precluded, denoting correct seating of the proximal end 2 of the catheter 1 within the connector assembly 3. At this time, the segments 4, 5 are respectively compressed, making use of the finger grips 8, 19 as desired, until such time as the rib 23 of the body 20 engages the detent 17 of the body 7 (FIG. 3), denoting the assembled position of the connector assembly 3. This differential in respective positioning between the segments 4, 5 will cause selective compression of the plug 6 within the cavity 35, which compression causes constriction of the channel 38 and thereby secures the catheter 1 within the connector assembly 3.

It will be noted that overtightening and undertightening of the plug 6 around the catheter 1 is prevented since closure of the connector assembly 3 is regulated by means of the spacing which is provided between the detents 16, 17. Thus, bringing the rib 23 in contact with the detent 17 assures a secure, yet unoccluded engagement of the catheter 1 within the connector assembly 3. In addition, the tapers of the shaped ends 37 of the plug 6 cooperate with the configuration of the cavity 35 to develop a constriction along the length of the channel 38 which is essentially uniform, preventing undesirable catheter occlusion resulting from uneven compression of the plug 6. The snap-fit interengagement developed enables the foregoing results to be accomplished automatically using a single hand, and without using threaded components, further enhancing the capabilities of the connector assembly 3. Upon assembly, the connector assembly 3 is then ready for use in combination with an appropriate connector 26, as desired, interconnection between the connector assembly 3 and the connector 26 being facilitated by means of the lugs 27 associated with the segment 5. Although disassembly of the connector assembly 3 is generally not called for, and is to be avoided, it should be noted that the connector assembly 3 is capable of disassembly by reversing the foregoing procedure, should such disassembly ever become necessary.

It will therefore be seen that the connector assembly 3 serves well to satisfy each of the objectives previously set forth. It will also be understood that the connector assembly 3 is capable of variation without departing from the spirit and scope of the present invention.

For example, the structural configuration of the connector assembly 3 may be varied in several ways. Size, configuration, and location of the finger grips 8, 19 along the bodies 7, 20 of the segments 4, 5 of the connector assembly 3 may be varied, or even omitted, as may the positioning and number of the guides 19 which project from the edge 18 of the body 7, provided the cooperating slots 42 of the body 20 are correspondingly configured. Also capable of variation is the overall size and outer configuration of the bodies 7, 20, provided the bodies 7, 20 are correspondingly configured for telescoping cooperation as described above; the structuring of the end 25 of the segment 5 which engages the connector 26 of the medical device used in connection with the catheterization procedure; and the structuring of the means which are used to develop a snap-fit relationship between the segments 4, 5, apart from the cooperating ribs and detents described.

It will also be understood that the various diameters of the opening 11 of the segment 4, the opening 30 of the segment 5, and the channel 38 of the plug 6 may be suitably varied to accommodate catheters having different outer diameters, provided the stop 31 is correspondingly configured to engage the proximal end of the catheter used, as described above, while assuring the passage of fluid through the channel 32 and into the cavity 33. Color coding of the segments 4, 5 and the plug 6 may be used to facilitate the selection of components which are appropriate for use with the catheter selected, if desired.

Lastly, although tapered, symmetrical shaping of the plug 6 as previously described is preferred, it is to be understood that other tapers may be provided in combination with correspondingly configured cavities 35, or differently configured cavities 35 developed upon interconnecting the segments 4, 5. It is even possible, although less desirable, to use cylindrical plugs 6 in combination with a cylindrical cavity 35 and a snap-fit arrangement in accordance with the present invention, or even an assymetrical plug 6. However, such use may result in a loss of uniformity in constriction of the channel 38 of the plug 6 depending upon the configuration used.

It will therefore be understood that various changes in the details, materials and arrangement of parts which have been herein described and illustrated in order to explain the nature of this invention may be made by those skilled in the art within the principle and scope of the invention as expressed in the following claims, and that the present invention will find applicability in forming tubular connections apart from catheterizations and medical procedures, if desired.

What is claimed is:

1. An adaptive connector for engaging a tubular member, comprising:
   a pair of segments adapted for telescoping engagement with one another, said segments combining to develop a centrally disposed cavity, and at least one of said segments having an opening in an end thereof which communicates with said cavity and which is adapted to receive said tubular member therein; and
   a plug formed of a compressible material and located within said cavity, said plug having a channel extending longitudinally therethrough for receiving said tubular member from said opening;
   said cavity and said plug having cooperating surfaces for compressing said plug and for applying substantially uniform forces against said tubular member along the length of said member receiving channel to uniformly constrict said channel about said tubular member and thereby securely engage said tubular member within said adaptive connector when said telescoping segments are engaged with one another.

2. The connector of claim 1 wherein said segments are generally tubular in peripheral shape and are sized to slidingly engage each other.

3. The connector of claim 2 wherein said tubular segments are cylindrical.

4. The connector of claim 1 wherein another end of said segments includes connector means for connecting an external device to said adaptive connector.

5. The connector of claim 4 wherein said connector means and said opening are at opposite ends of said telescoping segments.

6. The connector of claim 4 wherein said connector means includes lug means for engaging said external device to said connector means.

7. The connector of claim 4 wherein a channel is formed in said telescoping segments which communicates between said connector means and said cavity.

8. The connector of claim 7 wherein the channel of said telescoping segments and said opening are in substantial alignment with one another.

9. The connector of claim 7 wherein the channel of said telescoping segments is adapted to receive said tubular member.

10. The connector of claim 9 wherein the channel of said telescoping segments includes stop means for limiting penetration of said tubular member into said channel.

11. The connector of claim 10 wherein said opening and the channel of said telescoping segments are sized to slidingly receive said tubular member.

12. The connector of claim 7 wherein the channel of said plug is in substantial alignment with the channel of said telescoping members.

13. The connector of claim 12 wherein said channels are axially aligned.

14. The connector of claim 7 wherein said opening is a channel.

15. The connector of claim 14 wherein said channels are in axial alignment.

16. The connector of claim 1 wherein said opening comprises guide portions which diverge from said opening to the associated end of said telescoping members.

17. The connector of claim 1 wherein said connector further comprises finger grip means extending from an outer surface of said telescoping segments.

18. The connector of claim 17 wherein an opposed pair of finger grips extend from said outer surface.

19. The connector of claim 18 wherein a plurality of finger grip pairs extend from said telescoping segments.

20. The connector of claim 19 wherein said finger grip pairs extend from each of said telescoping segments.

21. The connector of claim 1 wherein said telescoping segments comprise an inner and an outer segment, and wherein guide means extend from said outer segment and along said inner segment.

22. The connector of claim 21 wherein said guide means engage a slot formed in the outer surface of said inner segment.

23. The connector of claim 22 wherein said guide means are axially aligned and radially offset.

24. The connector of claim 1 wherein said plug receiving cavity is generally cylindrical at its center and terminates at tapered ends.

25. The connector of claim 24 wherein said cavity is symmetrical.

26. The connector of claim 1 wherein said plug receiving cavity and said plug are correspondingly configured.

27. The connector of claim 1 wherein said tubular member is a catheter.

28. The connector of claim 1 wherein said plug is formed of an elastomeric material.

29. The connector of claim 28 wherein said plug is radially symmetrical.

30. The connector of claim 29 wherein said plug is axially symmetrical.

31. The connector of claim 28 wherein terminal portions of said channel are chamfered.

32. The connector of claim 28 wherein said plug is essentially cylindrical at the center and tapered at the ends.

33. The connector claim of claim 32 wherein said plug is configured so that, upon compression of said plug, said constriction about said tubular member is substantially uniform substantially fully along the length of said channel.

34. The connector of claim 1 having means for developing a snap-fit engagement between said telescoping segments.

35. The connector of claim 1 wherein said telescoping segments are longitudinally compressed, without respective rotation, to compress said plug and constrict said channel without torsion.

36. The connector of claim 35 wherein said adaptive connector includes means for preventing respective rotation between said pair of telescoping segments.

37. The connector of claim 36 wherein said telescoping segments comprise an inner and an outer segment, and wherein guide means extend from said outer segment and along the surface of said inner segment, to engage a slot formed in the outer surface of said inner segment.

38. The connector of claim 34 wherein said snap-fit engagement developing means comprises a plurality of detents associated with the surface of one of said segments, and a ring projecting from the surface of the other of said segments for selective engagement within said detents.

39. The connector of claim 38 having at least two detents, wherein a first detent cooperates with said ring to develop a stand-by position, and wherein a second detent cooperates with said ring to develop an operative position.

40. The connector of claim 39 wherein said plug essentially completely fills said cavity, but is not compressed, in said stand-by position.

41. The connector of claim 40 wherein said plug is compressed in said operative position.

42. The connector of claim 41 wherein said detents are spaced, and wherein said spacing develops the degree of said compression.

43. The connector of claim 43 wherein said degree of compression is sufficient to engage said tubular member within said adaptive connector, and insufficient to occlude said tubular member.

44. An adaptive connector for engaging a tubular member having a hollow center which is not to be occluded, comprising:
   a pair of segments adapted for telescoping engagement with one another, wherein said segments combine to develop a centrally disposed, generally symmetrical cavity which is cylindrical at its center and which terminates at tapered ends, and wherein at least one of said segments has an opening in an end thereof which communicates with said cavity and which is adapted to receive said tubular member therein;
   a plug formed of a compressible material and located within said cavity, wherein said plug and said plug receiving cavity are correspondingly configured, and wherein said plug has a channel extending longitudinally therethrough for receiving said tubular member from said opening; and
   means for compressing said plug and for applying substantially uniform forces against said tubular member along the length of said member receiving channel to uniformly constrict said channel about said tubular member and securely engage said tubular member within said adaptive connector, comprising means for developing a snap-fit engagement between said telescoping segments so that when said telescoping segments are engaged, said plug is automatically placed in compression so that said plug is substantially uniformly constricted about said tubular member along the length of said member receiving channel, without occluding the hollow center of said tube.

* * * * *